(12) United States Patent
Pepper et al.

(10) Patent No.: US 9,802,027 B2
(45) Date of Patent: *Oct. 31, 2017

(54) SEMI-COMPLIANT MEDICAL BALLOON

(71) Applicant: BARD PERIPHERAL VASCULAR, INC., Tempe, AZ (US)

(72) Inventors: Lanny R. Pepper, Larue, TX (US); William F. Davies, Jr., Athens, TX (US)

(73) Assignee: BARD PERIPHERAL VASCULAR, INC., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/264,150

(22) Filed: Sep. 13, 2016

(65) Prior Publication Data

US 2016/0375228 A1 Dec. 29, 2016

Related U.S. Application Data

(63) Continuation of application No. 14/551,165, filed on Nov. 24, 2014, now abandoned, which is a continuation of application No. 12/483,636, filed on Jun. 12, 2009, now Pat. No. 8,900,215.

(51) Int. Cl.
*A61M 25/00* (2006.01)
*A61M 25/10* (2013.01)

(52) U.S. Cl.
CPC ..... *A61M 25/10* (2013.01); *A61M 2025/1075* (2013.01); *A61M 2025/1084* (2013.01)

(58) Field of Classification Search
None
See application file for complete search history.

(56) References Cited

U.S. PATENT DOCUMENTS

| | | | | |
|---|---|---|---|---|
| 4,637,396 A | * | 1/1987 | Cook | A61M 25/10 604/103 |
| 4,702,252 A | * | 10/1987 | Brooks | A61M 25/0108 604/103 |
| 4,706,670 A | * | 11/1987 | Andersen | A61L 29/06 604/526 |
| 4,796,629 A | * | 1/1989 | Grayzel | A61M 25/104 604/103.09 |
| 4,820,349 A | * | 4/1989 | Saab | A61M 25/1029 604/913 |
| 4,834,755 A | * | 5/1989 | Silvestrini | A61F 2/06 623/1.53 |

(Continued)

*Primary Examiner* — Scott Medway
(74) *Attorney, Agent, or Firm* — King & Schickli, PLLC

(57) ABSTRACT

A semi-compliant fiber-reinforced medical balloon having a folded wall thickness of from about 0.0010 to about 0.0060 inches and a rated burst pressure of at least 15 atmospheres and exhibiting compliance in the radial direction of from 0.5% expansion per atmosphere to rated burst pressure of the balloon includes a base balloon formed from a semi-elastic polymer about 1.0% expansion per atmosphere when pressurized from a fully inflated diameter to the material having an elongation to break of from about 10% to about 20%, a fiber layer is disposed over the base balloon with fibers having an elongation to break of from about 10% to about 20% and an outer layer formed from a semi-elastic polymer material having an elongation to break of from about 10% to about 20% disposed over the fiber layer.

20 Claims, 7 Drawing Sheets

(56) References Cited

U.S. PATENT DOCUMENTS

| | | | | |
|---|---|---|---|---|
| 4,906,244 A * | 3/1990 | Pinchuk | A61L 29/06 | 604/913 |
| 5,112,304 A * | 5/1992 | Barlow | A61M 25/104 | 604/103.09 |
| 5,116,360 A * | 5/1992 | Pinchuk | A61F 2/06 | 623/1.39 |
| 5,290,306 A * | 3/1994 | Trotta | A61M 25/10 | 604/103.01 |
| 5,304,340 A * | 4/1994 | Downey | A61M 25/1029 | 264/521 |
| 5,477,886 A * | 12/1995 | Van Beugen | B29C 53/602 | 138/89 |
| 5,620,649 A * | 4/1997 | Trotta | A61M 25/10 | 264/515 |
| 5,629,077 A * | 5/1997 | Turnlund | A61F 2/82 | 156/308.2 |
| 5,647,848 A * | 7/1997 | Jørgensen | A61M 25/104 | 604/103.11 |
| 5,741,325 A * | 4/1998 | Chaikof | A61F 2/90 | 623/1.35 |
| 5,752,934 A * | 5/1998 | Campbell | A61L 29/085 | 604/96.01 |
| 5,772,681 A * | 6/1998 | Leoni | A61M 25/005 | 606/192 |
| 5,820,613 A * | 10/1998 | Van Werven-Franssen | A61M 25/104 | 604/103.09 |
| 5,868,779 A * | 2/1999 | Ruiz | A61M 25/104 | 606/192 |
| 6,010,480 A * | 1/2000 | Abele | A61F 2/958 | 604/103.06 |
| 6,146,356 A * | 11/2000 | Wang | A61L 29/06 | 604/96.01 |
| 6,164,283 A * | 12/2000 | Lesh | A61B 18/1492 | 128/898 |
| 6,183,492 B1 * | 2/2001 | Hart | A61B 17/12036 | 604/96.01 |
| 6,263,236 B1 * | 7/2001 | Kasinkas | A61B 18/24 | 604/21 |
| 6,746,425 B1 * | 6/2004 | Beckham | A61L 29/126 | 604/103.09 |
| 6,749,614 B2 * | 6/2004 | Teitelbaum | A61B 17/1671 | 606/250 |
| 6,905,743 B1 * | 6/2005 | Chen | A61L 29/049 | 264/108 |
| 6,942,680 B2 * | 9/2005 | Grayzel | A61F 2/958 | 606/159 |
| 6,977,103 B2 * | 12/2005 | Chen | A61L 29/126 | 264/108 |
| 7,252,650 B1 * | 8/2007 | Andrews | A61F 2/958 | 604/103.06 |
| 7,354,419 B2 * | 4/2008 | Davies, Jr. | A61M 25/104 | 604/103.06 |
| 7,435,254 B2 * | 10/2008 | Chouinard | A61F 2/90 | 623/1.15 |
| 7,682,335 B2 * | 3/2010 | Pepper | A61L 29/085 | 604/103.09 |
| 8,002,744 B2 * | 8/2011 | Pepper | A61M 25/10 | 604/103.06 |
| 8,702,679 B2 * | 4/2014 | Deckman | A61M 25/0045 | 604/523 |
| 2001/0000188 A1 * | 4/2001 | Lenker | A61F 2/07 | 623/1.13 |
| 2002/0098307 A1 * | 7/2002 | Schwartz | A61L 29/14 | 428/36.3 |
| 2002/0132072 A1 * | 9/2002 | Wang | A61L 29/06 | 428/35.2 |
| 2003/0100916 A1 * | 5/2003 | Lee | A61M 25/1027 | 606/194 |
| 2003/0149468 A1 * | 8/2003 | Wallsten | A61M 25/104 | 623/1.11 |
| 2004/0006359 A1 * | 1/2004 | Laguna | A61M 25/1002 | 606/192 |
| 2005/0271844 A1 * | 12/2005 | Mapes | A61L 29/048 | 428/36.1 |
| 2006/0008606 A1 * | 1/2006 | Horn | A61L 29/126 | 428/36.1 |
| 2006/0085022 A1 * | 4/2006 | Hayes | A61M 25/104 | 606/192 |
| 2007/0112370 A1 * | 5/2007 | Andrews | A61M 25/1029 | 606/194 |
| 2008/0097301 A1 * | 4/2008 | Alpini | A61M 25/1029 | 604/103.07 |
| 2008/0097374 A1 * | 4/2008 | Korleski | A61B 17/8855 | 604/500 |
| 2008/0125710 A1 * | 5/2008 | Hobson | A61L 29/085 | 604/103.01 |
| 2008/0183132 A1 * | 7/2008 | Davies | A61M 25/104 | 604/103.09 |
| 2010/0010438 A1 * | 1/2010 | Simpson | A61M 25/10 | 604/96.01 |
| 2012/0004496 A1 * | 1/2012 | Farnan | A61M 1/3653 | 600/16 |

\* cited by examiner

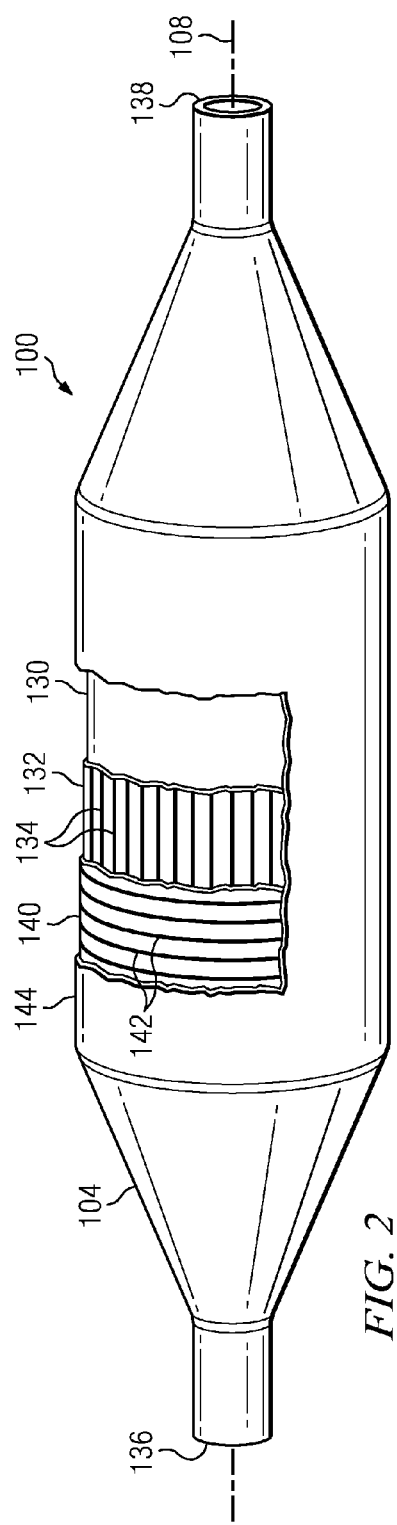
FIG. 2
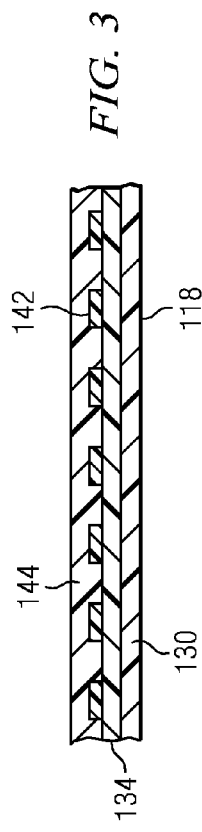
FIG. 3
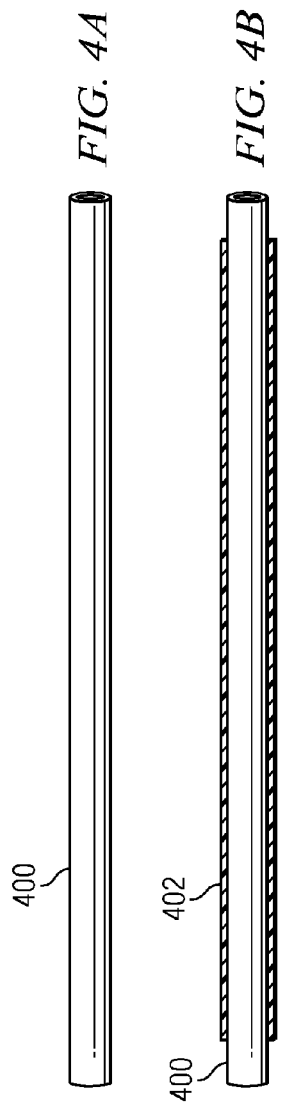
FIG. 4A
FIG. 4B

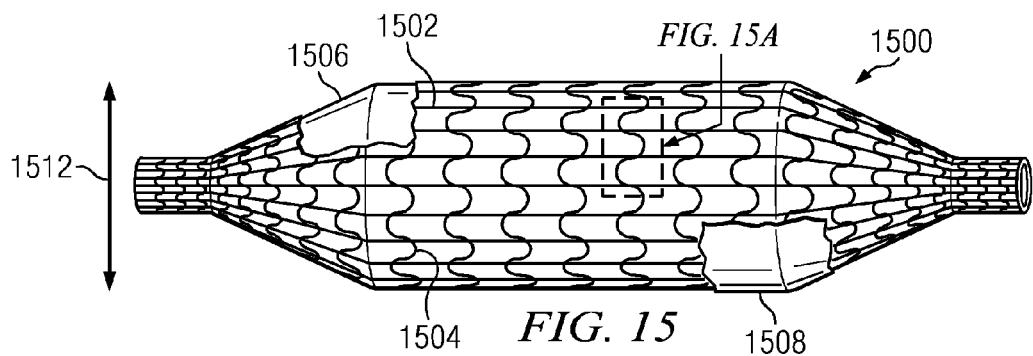
FIG. 15
FIG. 15A
FIG. 15B
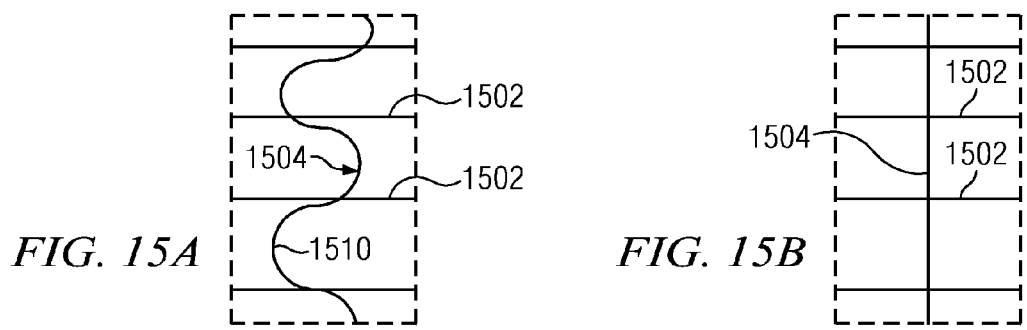
FIG. 16
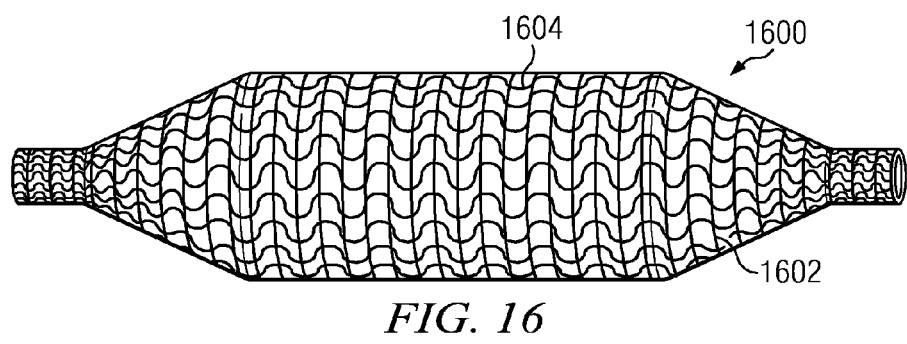
FIG. 17

SEMI-COMPLIANT MEDICAL BALLOON

This application is a Continuation of U.S. patent application Ser. No. 14/551,165, filed Nov. 24, 2014, which is a continuation of U.S. patent application Ser. No. 12/483,636, filed Jun. 12, 2009, now issued U.S. Pat. No. 8,900,215, issued Dec. 2, 2014, entitled "SEMI-COMPLIANT MEDICAL BALLOON", the disclosures of which are incorporated herein by reference.

TECHNICAL FIELD

This disclosure relates to medical dilation balloons; and, in particular, it relates to semi-compliant medical balloons useful in angioplasty, stent placement and dilation and other medical applications including cardiology, radiology, urology and orthopedics.

BACKGROUND

Non-compliant medical balloons for performing angioplasty and other medical procedures are known. U.S. Pat. No. 6,746,425 to Beckham discloses a non-compliant medical balloon and methods for manufacturing the balloon. U.S. Patent Application Publication No. US 2006/0085022 to Hayes et al. discloses a non-compliant medical balloon having an integral woven fabric layer and methods for manufacturing the balloon. U.S. Patent Application Publication No. US 2006/0085023 to Davies, Jr. et al. discloses a medical balloon having strengthening rods and methods for manufacturing the balloon. U.S. Patent Application Publication No. US 2006/0085024 to Pepper et al. discloses a non-compliant medical balloon having an integral nonwoven fabric layer and methods for manufacturing the balloon. U.S. Pat. No. 6,746,425 and Publication Nos. US 2006/0085022, US 2006/0085023 and US 2006/0085024 are hereby incorporated herein by reference.

Medical balloons are widely used in a variety of medical procedures. Typically, an uninflated medical balloon is inserted into a body-space, e.g., blood vessel, urological vessel, etc. by means of a catheter. After positioning at the desired location within the body, the medical balloon may be inflated by introducing a pressurized fluid into the balloon through the catheter. The pressurized fluid causes the medical balloon to expand, and the adjacent body-space is similarly expanded. The fluid may then be withdrawn from the balloon, causing it to collapse to facilitate its removal from the body. Medical balloons are also used for temporarily occluding vessels, placing medical devices such as stents, drug delivery and heat transfer.

Medical balloons are generally referred to as compliant, non-compliant and semi-compliant. Balloon compliance is a term used to describe the change in a balloon's diameter as a function of pressure. Low pressure compliant medical balloons are typically formed from elastomers such as latex, polyurethane and other thermoplastic elastomers. Low pressure compliant medical balloons may expand by 100% or greater upon inflation. Compliant medical balloons are typically used for fixation and occlusion.

Alternatively, high pressure non-compliant dilation balloons expand very little, if at all, when pressurized from a nominal diameter to a rated burst pressure. The rated burst pressure is the maximum pressure at which there is a statistical 95% confidence level that 99.9% of the population of balloons will not burst. High pressure non-compliant balloons may have rated burst pressures of up to 20 atmospheres or higher. Generally, high pressure, non-compliant balloons are formed from relatively inelastic materials such as oriented highly crystalline polyethylene terephthalate (PET) films. Such PET films provide high tensile strength, and may be used to form balloons with thin walls having high burst pressures. However, balloons formed from PET and similar materials having a high strength relative to wall thickness tend to be more susceptible to puncture. Balloons formed from PET also tend to be stiffer than balloons made from other more compliant materials. The stiffness of the deflated balloon directly affects its "trackability," i.e., its ability to traverse sharp turns or branches of the vessels or body cavities through which the balloon must pass. Balloons having more flexible walls generally provide better trackability.

The term "semi-compliant" is used herein to describe a balloon that exhibits a moderate degree of expansion when pressurized from its operating pressure (e.g. the pressure at which the balloon reaches its nominal diameter) to its rated burst pressure. In some applications a semi-compliant balloon may be more desirable than a non-compliant balloon. Semi-compliant balloons tend to be less stiff than semi-compliant balloons, resulting in better trackability. Semi-compliant balloons may also provide better puncture resistance than non-compliant balloons. Thus, a practitioner may prefer a semi-compliant balloon over a non-compliant balloon in procedures where the balloon must be used to expand a hard or calcified stenosis or where the balloon must be threaded through small diameter blood vessels, and/or where the balloon has to traverse a torturous path. In some instances, a semi-compliant dilation balloon may be used to pre-dilate a stenosis before stent placement. A practitioner may also prefer a semi-compliant dilation balloon over a non-compliant balloon for stent placement and/or for post-stent dilation.

Dilation balloons are often used to open or expand open body spaces restricted by tough tissues such as strictures, scarring or calcified areas. In these applications medical dilation balloons having high operating and burst pressures may be required. For example, dilation balloons are used in angioplasty, a procedure in which the balloon may be used to expand a stenoic lesion. In these applications it is desirable to make the outer wall of the dilation balloon as thin as possible while still maintaining the required pressure rating or burst strength. It is also desirable that the balloon exhibit a high degree of puncture resistance.

In order to reduce the profile of the balloon, dilation balloons may be formed with pleated walls. When the balloon is deflated (i.e., before or after inflation), these pleats are folded over, wrapped and/or rolled around the long axis of the balloon. Consequently, the thinner the wall material of the balloon, the smaller the diameter of the balloon-catheter assembly. A smaller diameter may be used with a smaller introducer, reducing patient discomfort. A smaller diameter also facilitates passage of the deflated balloon through narrow vessels, lumens or cavities of the body prior to deployment.

Semi-compliant balloons may be produced from materials such as nylon which is softer than PET and provides moderate compliance and improved trackability. However, the tensile strength of nylons suitable for fabricating medical dilation balloons is typically less than that of PET. Thus, a dilation balloon formed from a nylon or similar semi-elastic material would require thicker walls in order to achieve the same burst pressures as PET dilation balloons. This in turn increases the diameter of the balloon catheter assembly and the size of the introducer used in the procedure. Thus, there exists a need for dilation balloons having a moderate level of compliance, puncture resistance, high burst pressures and thin walls.

SUMMARY

In one aspect, a semi-compliant fiber-reinforced medical balloon that may be inflated and deflated, and when inflated exhibits a moderate change in radial distension across a predetermined range of internal pressures includes a generally cylindrical barrel wall disposed between tapered cone walls and cylindrical neck walls extending therefrom along a longitudinal axis. The fiber-reinforced balloon may include a base balloon formed from a semi-elastic polymer material having an elongation to break of from about 10% to about 20% and wherein the base balloon defines the cylindrical barrel wall, tapered cone walls and cylindrical neck walls. In one variation, a first fiber layer is disposed over the base balloon with fibers having an elongation to break of from about 10% to about 20%. An outer layer formed from a semi-elastic polymer material having an elongation to break of from about 10% to about 20% is disposed over the first fiber layer. The balloon has a rated burst pressure of at least 15 atmospheres and exhibits compliance in the radial direction of from 0.5% expansion per atmosphere to about 1.0% expansion per atmosphere when pressurized from a fully inflated diameter to the rated burst pressure of the balloon. The balloon may be configured to have a folded wall thickness of from about 0.0010 to about 0.0060 inches.

The semi-compliant fiber-reinforced medical balloon may include a plurality of substantially semi-elastic fibers extending longitudinally from one neck wall to the opposite neck wall along the longitudinal axis of the balloon with the fibers being substantially equally spaced apart around the circumference of the balloon. In other variations, the first fiber layer may be one of a woven, knitted, non-woven or braided fiber material. The fibers of the first fiber layer may have a thickness from about 0.0005 to about 0.025 inch and width-to-thickness ratio in the range from about 25:1 to about 45:1.

In another embodiment, the semi-compliant fiber-reinforced medical balloon may include a second fiber layer disposed over the first fiber layer. The fibers of the second fiber layer may be semi-elastic hoop fibers wrapped circumferentially around the balloon from one neck or cone wall to the opposite neck or cone wall such that the hoop fibers are substantially transverse to the longitudinal axis of the balloon. In other variations, the second fiber layer may be one of a woven, knitted, non-woven or braided fiber material.

In another aspect, a fiber-reinforced medical balloon that may be inflated and deflated, includes a generally cylindrical barrel wall disposed between tapered cone walls and cylindrical neck walls extending from the cone walls along the longitudinal axis of the balloon. The balloon may include first and second fiber layers, the fibers of the first fiber layer being substantially inelastic and defining the cylindrical barrel wall, tapered cone walls and cylindrical neck walls. In this regard, the fibers of the first fiber layer may extend longitudinally from one cone wall to the opposite cone wall along the longitudinal axis of the balloon with the fibers being substantially equally spaced apart around the circumference of the balloon. A second fiber layer may be disposed over the first fiber layer. In one variation, the fibers of the second fiber layer are semi-elastic and have an elongation to break of from about 10% to about 20%. An outer layer formed from a semi-elastic polymer material having an elongation to break of from about 10% to about 20% may be disposed over the second fiber layer. In one embodiment, the balloon has a rated burst pressure of at least 15 atmospheres and exhibits a compliance of from 0.5% expansion per atmosphere to about 1.0% expansion per atmosphere in a radial direction when pressurized from a fully inflated diameter to the rated burst pressure of the balloon.

In different variations, the second fiber layer may be semi-elastic hoop fibers wrapped circumferentially around the balloon from one cone or neck wall to the opposite cone or neck wall such that hoop fibers are substantially transverse to the longitudinal axis of the balloon. The hoop fibers may have a thickness from about 0.0005 to about 0.025 inch and width-to-thickness ratio in the range from about 25:1 to about 45:1. In yet other embodiments, the second fiber layer may be one of a woven, knitted, non-woven or braided fiber material.

BRIEF DESCRIPTION OF THE DRAWINGS

For a more complete understanding, reference is now made to the following description taken in conjunction with the accompanying Drawings in which:

FIG. 2 is a partial cut-away view of the balloon of FIG. 1A;

FIG. 3 illustrates a partial longitudinal cross-section through the barrel wall of the balloon of FIG. 1A;

FIG. 4A is a side view of a tubular mandrel for constructing a balloon according to the disclosure;

FIG. 4B is a partial sectional view of the tubular mandrel 4A wherein a tube of moldable material has been placed over the mandrel;

FIGS. 15, 15A and 15B illustrate the placement of fibers in a first alternate construction of a semi-compliant balloon, FIG. 15 being a side view of the balloon, FIG. 15A being an enlarged view of a section of the balloon when initially inflated, and FIG. 15B being an enlarged view of the same sections of the balloon when fully inflated;

FIG. 16 illustrates the placement of fibers in a second alternate construction of a semi-compliant balloon; and FIG. 17 illustrates the placement of fibers in a third alternate construction of a semi-compliant balloon.

DETAILED DESCRIPTION

Figure 1A:
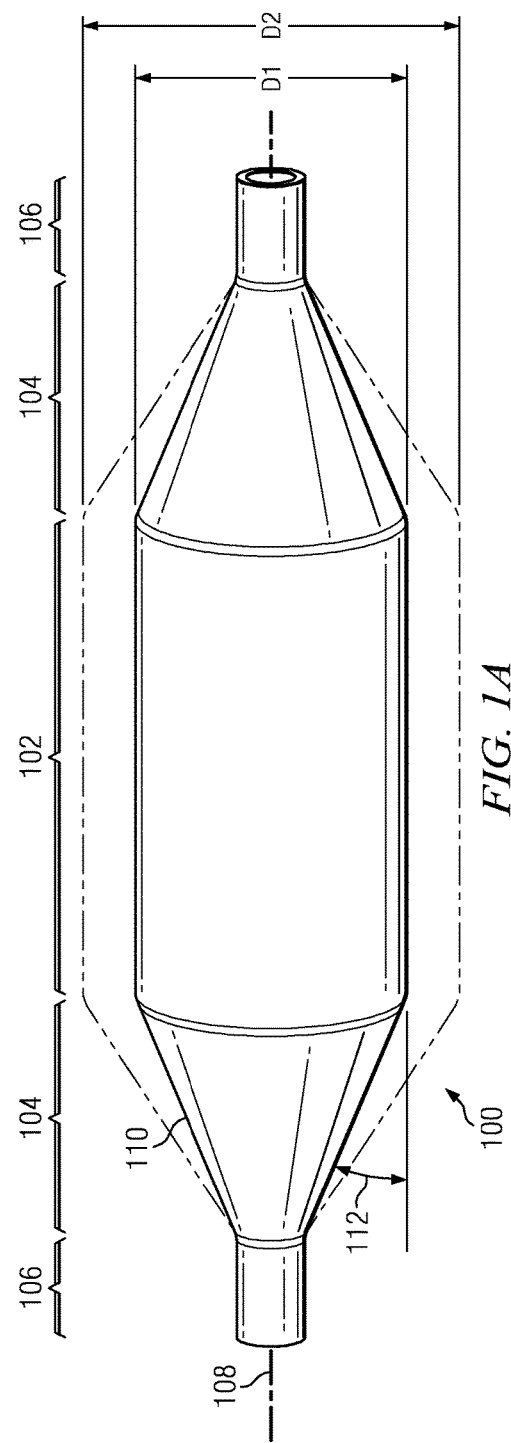
FIG. 1A is a perspective view of a semi-compliant balloon according to the disclosure.

Referring now to the drawings, wherein like reference numbers are used herein to designate like elements throughout, the various views and embodiments of semi-compliant medical balloons are illustrated and described, and other possible embodiments are described. The Figures are not necessarily drawn to scale, and in some instances the drawings have been exaggerated and/or simplified in places for illustrative purposes only. One of ordinary skill in the art will appreciate the many possible applications and variations based on the following examples of possible embodiments.

FIG. 1A is a side view of a fiber-reinforced semi-compliant medical dilation balloon according to one embodiment. As illustrated, medical balloon 100 is shown in a fully inflated state. Balloon 100 includes a generally cylindrical barrel portion 102 disposed between tapered cone portions 104 and cylindrical neck portions 106 extending from the cone portions along a longitudinal axis 108 of the balloon. The outer surface 110 of the cone portion 104 forms an angle 112 (the "cone angle") with respect to a longitudinal extension of the wall of the barrel portion 102. Higher cone angles generally provide a shorter total balloon length. In some embodiments, balloon 100 may have a cone angle 112 in the range of 12 degrees to 22 degrees, in others from 18 degrees to 22 degrees. In some embodiments, the cone angle 112 is about 20 degrees.

Figure 1B:
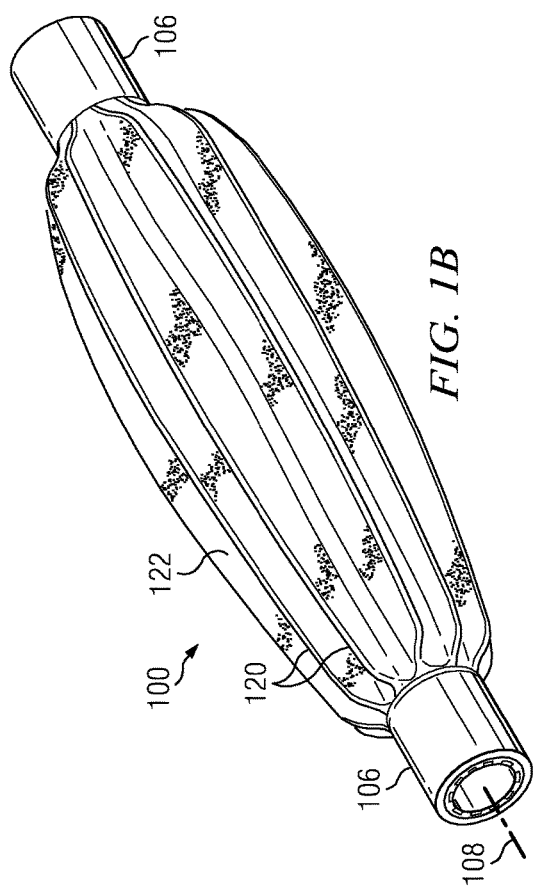
FIG. 1B is a perspective view of the balloon of FIG. 1A in a folded configuration.

Referring to FIG. 1B, balloon 100 is illustrated in a deflated state In its deflated state, the walls of barrel portion 102 and cone sections 104 of balloon 100 form pleats or folds 120 with creases 122 between the folds. As illustrated, folds 120 extend longitudinally from one neck portion 106 to the opposing neck portion 106. The pleated construction of the cone and barrel sections, 104, 106 reduces the diameter of balloon 100 to facilitate insertion of the balloon in its deflated state. Once positioned at the desired location, balloon 100 may be inflated through a catheter with a pressurized fluid such as a saline solution. As balloon 100 is inflated, folds and creases 120, 122 substantially disappear as the balloon reaches a fully inflated size having a nominal diameter D1 as illustrated in FIG. 1A.

Since balloon 100 is semi-compliant, further increases in the pressure of the fluid used to inflate the balloon (i.e., beyond the pressure needed to reach the nominal diameter D1) result in moderate further expansion (indicated by the broken line in FIG. 1A) to diameter D2. In one embodiment, semi-compliant balloon 100 expands at a rate of between 0.5% per atmosphere to about 1.0% per atmosphere over a terminal portion of its expansion range (e.g., expansion beyond its fully inflated diameter to its rated burst pressure). While balloon 100 may be constructed to any dimensions, balloons having a deflated diameter in the range from about 4 French Units (i.e., about 0.053 inches or 1.35 millimeters) to about 12 French Units (i.e., about 0.158 inches or 4.0 millimeters) are useful in the fields of cardiology, radiology, orthopedics and urology. In one embodiment, balloon 100 has a deflated diameter in the range of 4 to 12 French Units and a folded (e.g. when the balloon is deflated) wall thickness of from about 0.0010 to about 0.0060 inches.

FIG. 2 is a partial-sectional view of balloon 100, further illustrating the structure of the balloon. In one embodiment, balloon 100 includes a base layer or base balloon 130. Base balloon 130 is formed from a suitable semi-elastic polymer such as a nylon or a polyether block amide (PEBA) such as PEBAX® brand PEBA having a Shore D hardness from about 25 to about Shore D 54. In one embodiment, base balloon 130 has a double wall thickness of from about 0.0012 inches to about 0.0016 inches. Positioned over base balloon 130 is a first fiber layer 132 including a plurality of semi-elastic longitudinally extending fibers 134. As used herein, the term semi-elastic means a polymer material having an elongation to break of from about 10% to about 20%.

In one variation, fibers 134 are substantially the same length and extend from a first end 136 to a second end 138 of balloon 100. In other embodiments, fibers 134 may have different lengths. For example, one group of longitudinal fibers 134 may extend over the entire length of balloon 100 while another group of fibers may extend only over the length of barrel 102 or over the length of the barrel and partially over the cone. Longitudinally-oriented reinforcing fibers 134 may be oriented parallel or substantially parallel to one another and perpendicular within about 10 to 15 degrees to the balloon's longitudinal axis 108.

In one embodiment, fibers 134 may be attached to base balloon 130 with a suitable adhesive such as a polyurethane, a soluble, weldable polyamide material and/or embedded in a polymeric matrix. Fibers 134 may be selected from a semi-elastic material having an elongation to break of from about 10% to about 20% such as a high tenacity polyester or polyamide. Fibers 134 may have an elongation to break of from about 10% to about 20% to permit balloon 100 to expand moderately after reaching a nominal diameter.

In one embodiment, a second fiber layer 140 is positioned over first fiber layer 132. In one embodiment, second fiber layer 140 includes one or more semi-elastic hoop or circumferential reinforcing fibers 142. In one variation, one continuous hoop fiber 142 is wound over first fiber layer 132 from first end 136 to second end 138 of balloon 100. Circumferential reinforcing fibers 142 may be parallel or substantially parallel to one another and perpendicular within about 15 degrees to the longitudinally-oriented reinforcing fibers 134. In other embodiments, the second fiber layer may comprise a woven, non-woven, knitted or braided fiber material wherein the fibers are semi-elastic.

Fiber or fibers 142 may be secured in position with suitable adhesive such as a polyurethane, and/or embedded in a polymeric matrix. In one embodiment, fiber or fibers 142 are selected from a material having a moderate degree of compliance such as a high tenacity polyester or a high tenacity polyamide. In one variation fibers 134 are semi-elastic, e.g., selected to have an elongation to break of from about 10% to about 20% to permit balloon 100 to expand moderately after reaching a fully inflated state. In other embodiments, first and/or second fiber layers 132, 140 may be formed from a woven, braided, knitted or non-woven material as hereinafter described.

In the illustrated embodiment, balloon 100 includes an outer layer 144. Outer layer 144 may provide additional material to increase the puncture-resistance and surface smoothness of the balloon 100. Outer layer 144 may be formed from the same material as base balloon 130 or a different material. Outer layer 144 may be formed from a suitable polymer such as nylon or a polyether block amide such as PEBAX® brand PEBA. In one embodiment, base balloon 130 and outer layer 144 are formed from thermally-weldable polymer materials.

In one embodiment, to provide for moderate expansion beyond the fully inflated state, the materials from which base balloon 130, first fiber layer 132, second fiber layer 142 and outer layer 144 are selected to be physically compatible. For example, if base balloon 130 is too soft, (e.g. too elastic, low tensile strength) relative to the material of fibers 134 and 142, the base balloon may extrude and/or blow out between fibers 134 and 142 at less than the desired operating pressure. Alternatively, if the material of base balloon 130 is too hard (e.g. too inelastic, high tensile strength), the base balloon may fail prematurely and/or not provide the desired trackability and puncture resistance. Thus, the tensile properties (elasticity, tensile strength and elongation to break) of the materials used to form base balloon 130, longitudinal fibers 134 and hoop fibers 142 may be matched to prevent failure of the balloon while providing a high burst pressure and semi-compliance. Likewise, outer layer 144 should have suitable tensile properties (elasticity, tensile strength and elongation to break) sufficient to permit balloon 100 to expand moderately.

In other variations, it may be desirable to use substantially inelastic fibers for one of longitudinal fibers 134 and hoop fibers 142 to constrain expansion of balloon 100 in either a radial or longitudinal direction. For example, if longitudinal fibers 134 are formed from an inelastic or substantially inelastic material while hoop fibers 142 are made from a semi-elastic material, balloon 100 may expand moderately in a radial direction while linear expansion of the balloon would be constrained. Alternatively, if longitudinal fibers 134 are formed from a semi-elastic material with hoop fibers 142 formed from a substantially inelastic material, balloon 100 may expand in a longitudinal direction with expansion in a radial direction being constrained by the hoop fibers.

Thus, in one embodiment, the use of a combination of semi-elastic and substantially inelastic fibers may provide a balloon that is semi-compliant in a first direction and non-compliant in a second direction. In the case where one of longitudinal fibers 134 and hoop fibers 142 is semi-elastic with the other being substantially inelastic, balloon 100 may be non-compliant in a first direction (longitudinally or radially) and semi-compliant in a second direction perpendicular or substantially perpendicular to the first direction.

In the embodiments of balloon 100 wherein a combination of semi-elastic and substantially inelastic reinforcing fibers are used, the inelastic fibers may be Kevlar, Vectran, Spectra, Dacron, Dyneema, Turlon (PBT), Zylon (PBO), polyimide (PIM) and ultrahigh molecular weight polyethylenes In one variation, the inelastic reinforcing fiber may be a multi-filament Technora® brand paraphenylene/3,4-oxy-diphenylene/terephthalamide copolymer.

FIG. 3 is a partial longitudinal section of wall 118 of balloon 100 further illustrating construction of balloon 100. As illustrated longitudinal fibers 134 and hoop fibers 142 are ribbon shaped to reduce the thickness of wall 118 while maintaining the cross-sectional area of the fibers. In different embodiments, fibers 134, 142 may have a width-to-thickness ratio in the range from about 25:1 to about 45:1; in other variations the fibers may have a width-to-thickness ratio in the range from about 30:1 to about 40:1. In one embodiment, longitudinally oriented fibers 134 of the first fiber layer 140, have a fiber density generally about 15 to 30 fibers/inch having a fiber thickness of about 0.0005 to 0.025 inch and placed equidistant from one another will provide adequate strength in a longitudinal direction for a standard-sized semi-compliant medical balloon.

Fibers for use in balloon 100 may be supplied in the form of a bundle or "tow" of individual filaments. The tow typically has a generally circular cross-section and may include an adhesive to hold the filaments together and retain the cross-sectional shape of the tow. Before use in constructing balloon 100, the fiber tow may be drawn between one or more pair of closely spaced rolls to flatten the tow. A solvent or solvent-based adhesive may be applied to the tow before it is drawn between the roll to soften any adhesive and facilitate rearrangement of the filaments within the tow. After flattening, the fiber may be dried, if necessary, and used or stored for later use. The process of flattening the fibers is described in greater detail in co-pending U.S. application Ser. No. 12/187,259, filed Aug. 6, 2008 for a "Non-Compliant Medical Balloon," the disclosure of which is incorporated herein by reference for all purposes.

Turning to FIGS. 4A and 4B, in one embodiment, a removable tubular mandrel 400 may be used to assemble balloon 100. If balloon 100 is formed by stretch blow molding, mandrel 400 may be a tube of moldable material, such as a PET. A layer of moldable semi-elastic material 402 of moldable polymer such as nylon 6, nylon 6.6 Nylon 11 or Nylon 12 is placed over mandrel 400. Material 402 may be in the form of a tube as illustrated or as a film or tape wrapped around the mandrel. In other embodiments, material 402 may be applied in the form of a solution including the polymer that is applied to the mandrel by brushing, spraying or dipping. The tubular mandrel and the moldable material 402 may be stretch blow molded to the shape of the desired finished balloon, such as balloon 100 of FIG. 1.

Figure 5A:
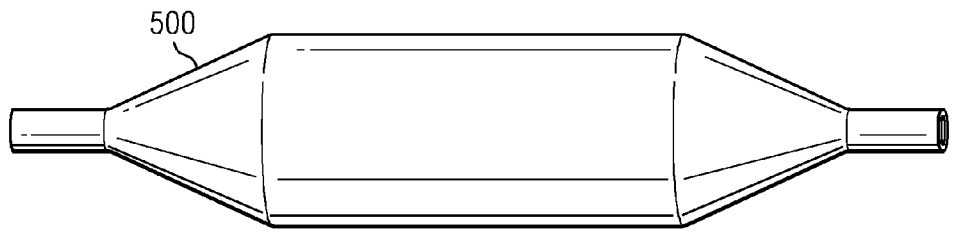
FIG. 5A is a side view of a preformed mandrel for constructing a balloon according to the disclosure.
Figure 5B:
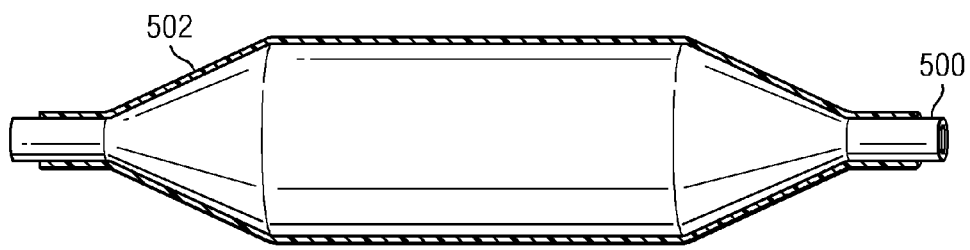
FIG. 5B is a partial sectional view of the preformed mandrel of 5A wherein a moldable material has been placed over the mandrel.

Turning to FIGS. 5A and 5B in another embodiment, a mandrel 500 may be a preform having the shape of the desired finished balloon as illustrated in FIG. 1A, in which case the mandrel may be a molded PET, a collapsible metal or polymeric foam, or formed from a wax or other low melting point material, or a material that may be removed by means of a solvent in subsequent processing. A layer of moldable semi-elastic material 502 of moldable polymer such as a poly-ether block amide, nylon 6, nylon 6.6 Nylon 11 or Nylon 12 is placed over mandrel 500. Material 502 may be in the form of a tube placed over the mandrel or film or tape wrapped around mandrel 500. In some variations, material 502 may be a polymer solution applied to mandrel 500 that is applied to the mandrel by brushing, spraying or dipping. In this variation, multiple layers of the solution may be applied to mandrel 502 to achieve the desired thickness, with or without heating and/or curing between applications of the solution.

Figure 6:
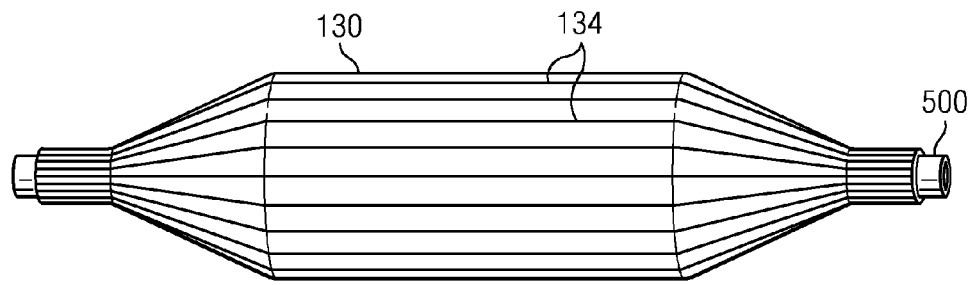
FIG. 6 illustrates the placement of a first fiber layer including longitudinally extending fibers over a base balloon.

FIG. 6 illustrates the placement of a first fiber layer 132 over base balloon 130. As illustrated, in one embodiment, after base balloon 130 is formed, a plurality of longitudinally oriented fibers 134 may be then be positioned on base balloon 130 to form first fiber layer 132. Longitudinally oriented fibers 134 may be applied to the base balloon by hand or mechanically. Mandrel 400 or 500 may be pressurized during the process to retain the desired shape as fibers 134 are applied over the base balloon. In one embodiment, an adhesive such as a urethane or a polymer solution may be applied to base balloon 130 and/or to fibers 134 to facilitate placement of fibers 134 on the base balloon, forming a fiber/polymer matrix upon curing. The adhesive or polymer solution, once cured, may be thermally-weldable to facilitate thermal bonding of the materials. In one embodiment, the solution is a soluble nylon in a solvent such as an alcohol. As illustrated, fibers 134 may be spaced equidistant apart and substantially parallel to longitudinal axis 108 and extend the length of base balloon 130. In one variation, from about 15 to about 30 fibers 134 per inch having a thickness from about 0.0005 to about 0.025 inch are used for balloons of 4 to 12 French.

Figure 7:
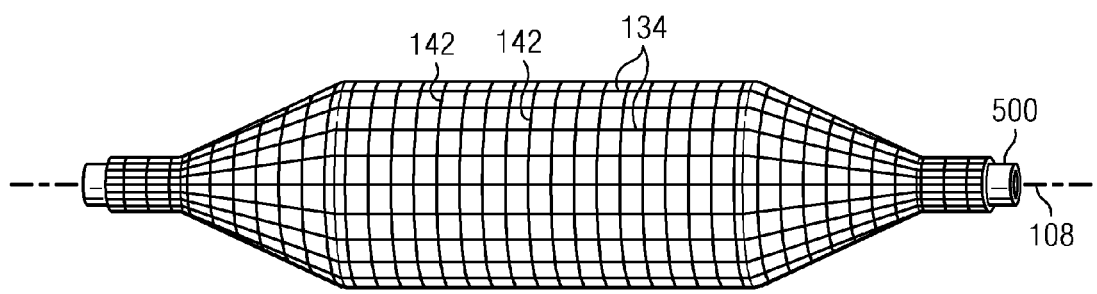
FIG. 7 illustrates the placement of circumferential or hoop extending fibers over a base balloon and first fiber layer to form a second fiber layer.

Referring now to FIG. 7, after longitudinally oriented fibers 134 have been applied to base balloon 130 and any curing, if necessary, has been done, one or more hoop fibers 142 are wound onto the base balloon. The fibers 142 of the second fiber layer 140 may be perpendicular to or substantially perpendicular to longitudinally oriented fibers 134 of first fiber layer 132. In one embodiment, circumferential fibers are perpendicular within about 10 to about 15 degrees of longitudinally oriented fibers 134. This transverse placement of hoop fibers 142 relative to longitudinal fibers 132 provides for radial stability of the fiber-reinforced balloon 100. Mandrel 400 or 500 may be pressurized during the process to retain the desired shape as hoop fibers 142 are applied over the first fiber layer.

Referring still to FIG. 7, hoop fibers 142 having a thickness of about 0.0005 to 0.025 inch may be wound over first fiber layer 132 at a rate of from about 30 to 80 wraps per inch in a generally parallel series of circumferential continuous loops to form second fiber layer 140. In another embodiment, hoop fibers 142 are wound over first fiber layer 132 at a rate of from 40 to about 60 wraps per inch in a substantially parallel series of circumferential continuous loops wherein the fiber is substantially perpendicular to the longitudinal axis of the balloon. In one variation, semi-elastic fibers hoop fibers 142 are wrapped circumferentially around the balloon from one neck wall to the opposite neck wall substantially transverse to the longitudinal axis of the balloon. In another embodiment, hoop fibers 142 are wrapped circumferentially around the balloon from one cone wall to the opposite cone wall.

In one embodiment, a ribbon shaped semi-elastic fiber 142 having a width of approximately 0.020 inches is wound at a rate of approximately 50 fibers per inch. An adhesive such as a urethane or a polymer solution, for example a soluble nylon in alcohol, may be applied to base balloon 130 to provide a "tacky" surface to facilitate placement of hoop fibers 142 on the base balloon. The soluble nylon will be incorporated into a fiber/polymer matrix upon curing. The adhesive or polymer solution, once cured, may be thermally-weldable to facilitate subsequent thermal processing and bonding of the layers together.

Figure 8:
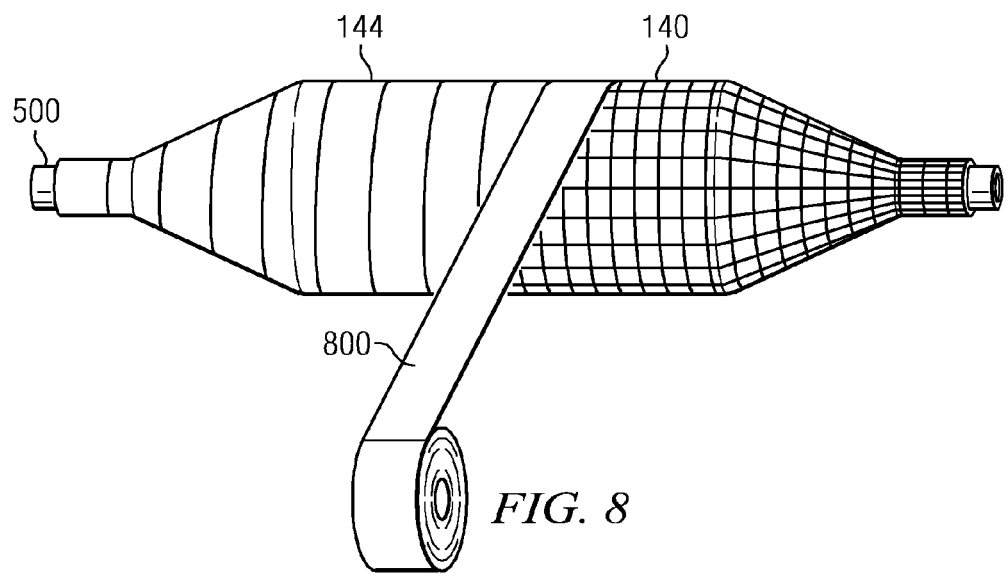
FIG. 8 illustrates one method of forming an outer layer over the first and second fiber layers illustrated in FIGS. 6 and 7.

Turning to FIG. 8 after second fiber layer 140 has been formed and any necessary curing has been done, an outer layer 144 may be applied over second fiber layer 140. Outer layer 144 may be applied as a film or a tape 800 wrapped over second fiber layer 140. An adhesive such as a urethane or a compatible polymer solution may be applied over second fiber layer or tape 800 to facilitate placement of outer layer 144. In one embodiment, the material of outer layer 144 is the same or a material similar to that used to form base balloon 130 so as to closely match the physical properties of the underlying materials. The material of outer layer 144 may be selected to be thermally or chemically weldable to the material of base balloon 130 to facilitate bonding of the layers. In other embodiments, outer layer 144 may be formed from a polymer solution applied by spraying, brushing or dipping the solution over second fiber layer 140.

In one embodiment, after outer layer 144 has been applied over second fiber layer 140 and allowed to cure, if necessary, mandrel 400 or 500 may be removed from balloon. In another embodiment, mandrel 400 or 500 with the base balloon 130, first and second fiber layers 132, 140 and outer layer 144 is placed into a die for heating. In some embodiments, mandrel 400 or 500 may be pressurized to conform the mandrel to the interior walls of the die. The die is then heated from about 300° F. to about 350° F. for a period from about 30 seconds to about 90 seconds to thermally weld one or more of the base balloon 130, first and second fiber layers 132, 140 and outer layer 144 together. In one embodiment, the die may be heated in an oven. Alternatively, the die may incorporate integral heating elements. In one variation, base balloon 130, outer layer 144 and any intervening layers or coatings are thermally welded together to encapsulate fibers 134 and 142 in a continuous polymer matrix.

Figure 9:
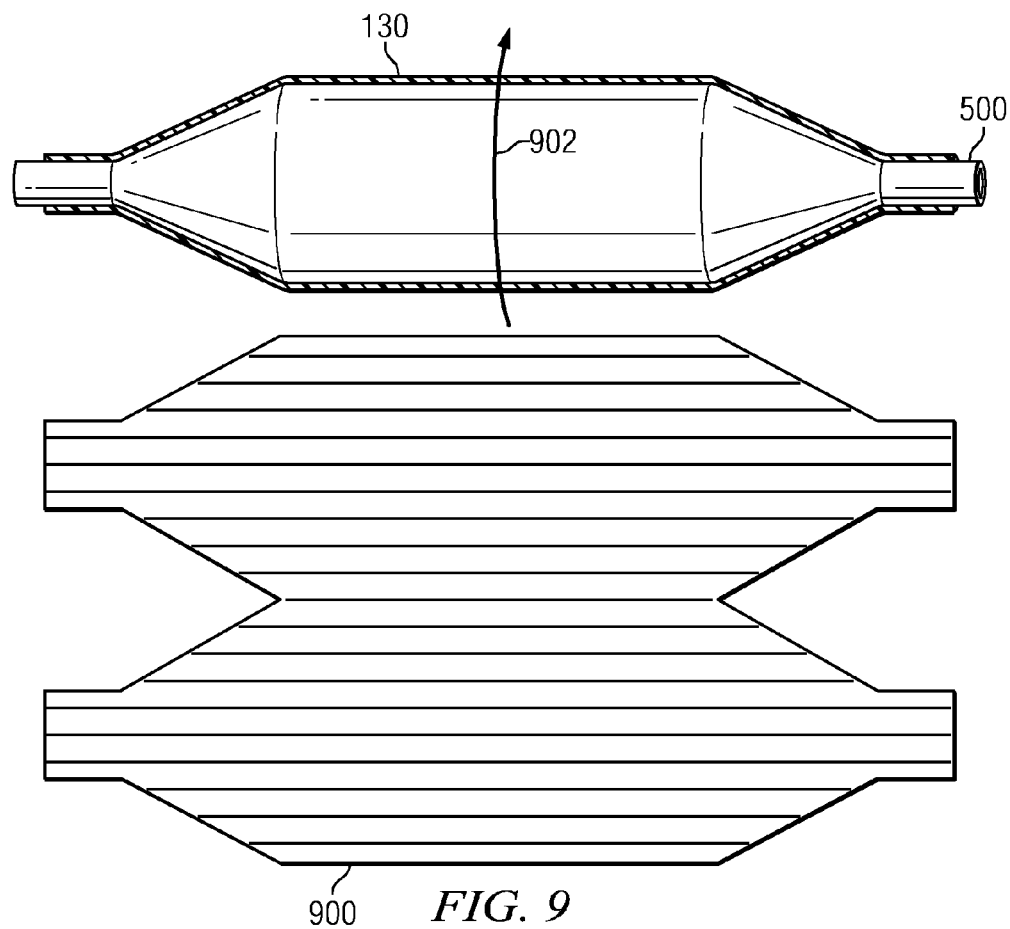
FIG. 9 illustrates an alternative method of forming a fiber layer.

Turning to FIG. 9, in an alternative embodiment, a first fiber layer 132 (FIG. 2) layer may be formed from a patterned sheet 900 of woven, non-woven, knitted or braided material formed from semi-elastic fibers. Patterned sheet 900 may be made as described in co-pending U.S. application Ser. No. 12/187,259, filed Aug. 6, 2008 for a "Non-Compliant Medical Balloon" except that sheet 900 may be formed from semi-elastic fibers rather than substantially inelastic fibers.

Figure 10:
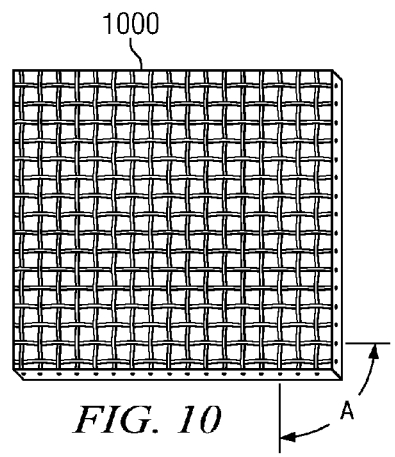
FIG. 10 illustrates a woven fiber material for forming a fiber layer.

FIG. 10 illustrates a woven material 1000 wherein fibers or filaments 1002 are interlaced. Fibers 1002 may be flattened prior to weaving as described above, or the woven material 1000 may be pressed, for example between rollers to achieve the desired thickness. In one variation, woven material 1000 may be coated with a thermally-weldable polymer, clamped between plates and heated to embed the fibers 1002 within the thermally-weldable polymer to produce a sheet having smooth surfaces. Alternatively, a film formed from a thermally-weldable polymer material may be placed over woven material 1000 and heated to encapsulate fibers 1002 in a polymer matrix.

As illustrated, the weave of material 1000 is shown with a high porosity, i.e., a relatively large amount of open space between fibers 1002. Other woven fabrics having greater or lesser porosities, including those having a very tight weave with essentially no porosity may be used in other embodiments. After fibers 1002 have been encapsulated into the wall of the balloon the angles (denoted "A") between the fibers preferentially remain constant when a balloon incorporating material 1000 is inflated and deflated.

Figure 11:
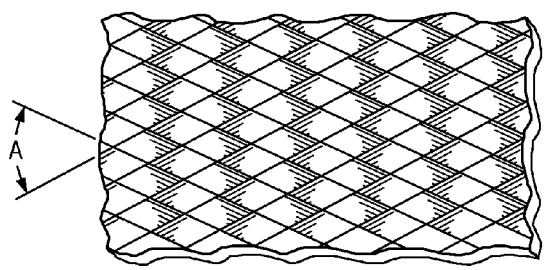
FIG. 11 illustrates a braided fiber material for forming a fiber layer.

FIG. 11 illustrates a braided material 1100 formed from semi-elastic fibers 1102. Braided material 1100 employs a fiber configuration in which three or more fibers are intertwined in such a way that no two fibers are twisted exclusively around one another. Braided material 1100 is formed from fibers 1102 that may be flattened before braiding. Alternatively, braided material 1100 may be otherwise processed to achieve the desired thickness. Braided material 1100 may be coated with a thermally-weldable polymer material and heated to embed fibers 1102 within a polymer matrix to produce sheet having uniform smooth surfaces. After material 1100 is incorporated into the wall of a balloon, such as medical balloon 100 of FIG. 1, fibers 1102 are encapsulated into the wall of the balloon such that the angles (denoted "A") between the fibers preferentially remain constant when a balloon incorporating material 1100 is inflated and deflated.

Figure 12:
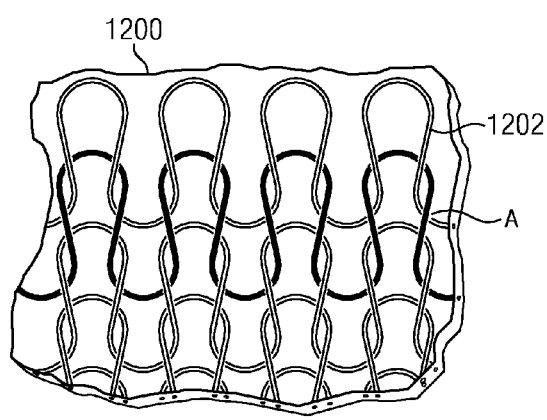
FIG. 12 illustrates a knitted fiber material for forming a fiber layer.
Figure 13:
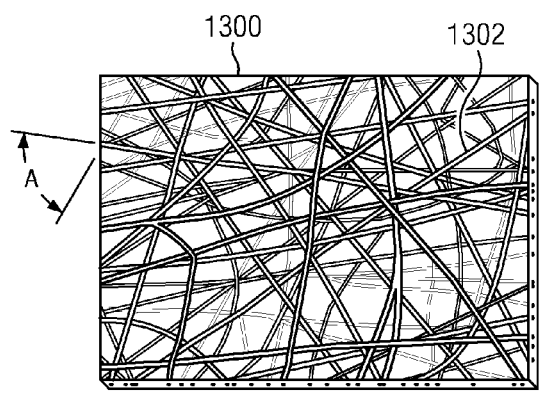
FIG. 13 illustrates a non-woven fiber material for forming a fiber layer.

FIGS. 12 and 13 illustrate a semi-elastic knitted material 1200 and a semi-elastic non-woven material 1300, respectively. Knitted material 1200 is produced by intertwining fibers 1202 in a series of interconnected loops 1204 rather than by weaving. In this fashion, loops 1204 of fibers 1202 are mechanically interlocked. A weft-knitted structure consists of horizontal, parallel courses of fibers and requires only a single fiber 1202. Alternatively, warp knitting requires one fiber 1202 for every stitch in the course, or horizontal row; these fibers make vertical parallel walls. In contrast, non-woven material 1300 are typically made from randomly-oriented fibers that are neither woven nor knitted. Fibers 1302 in non-woven fabrics typically have a web structure in which small fibers or filaments are held together by inter-fiber friction (e.g., matting), thermal binding (e.g., with a meltable binder) or chemical adhesion.

Knitted material 1200 or non-woven material 1300 may be embedded in a thermally-weldable polymer. In the case of the non-woven material 1300, the fibers 1302 may be randomly oriented, chopped fibers of the same or varying lengths that form random angles (denoted "A") at each fiber intersection. After the knitted material 1200 or non-woven material 1300 fibers 1200 and 1302 are incorporated into the wall of a medical balloon such as balloon 100 of FIG. 1, the fibers are embedded in a polymer matrix wherein the relative positions of the loops 1204 or angles (denoted "A") between fibers 1202 and 1302 preferably remains constant when a balloon incorporating materials 1200 and 1300 is inflated and deflated.

Referring again to FIG. 9, a patterned sheet 900 of knitted, braided, woven or non-woven material is wound around mandrel 500 over base balloon 130 as indicated by arrow 902 to form first fiber layer 132 (FIGS. 2 and 3). A layer or coating of an adhesive or thermally weldable polymer may be applied to base balloon 130 before winding patterned sheet 900 around the mandrel to facilitate placement of the sheet. In other embodiments, layers of knitted, braided, woven, non-woven patterned fiber sheets may be overlapped to provide multiple fiber layers. In yet other embodiments, base balloon 130 may be omitted wherein patterned sheet 900 is applied directly to mandrel 500 after which a second fiber layer and/or outer coating may be applied over the sheet.

After patterned sheet 900 has been positioned over base balloon 130, circumferential fibers may be wound around mandrel 500 over sheet 900 as illustrated in FIG. 7 to form second fiber layer 140. A layer or coating of an adhesive or thermally weldable polymer may be applied over patterned sheet 900 by means of spraying, brushing or dipping before circumferential fibers 142 are wound around the mandrel over the sheet to facilitate placement of the fiber or fibers. In other embodiments, second fiber layer 140 may be omitted. In still other embodiments, second fiber layer may be formed from a second patterned knit, woven, non-woven or braided material placed over sheet 900 on mandrel 500. After a second or subsequent fiber layer is formed, an outer layer 144 of polymeric material may be formed as described in connection with FIG. 8.

Figure 14:
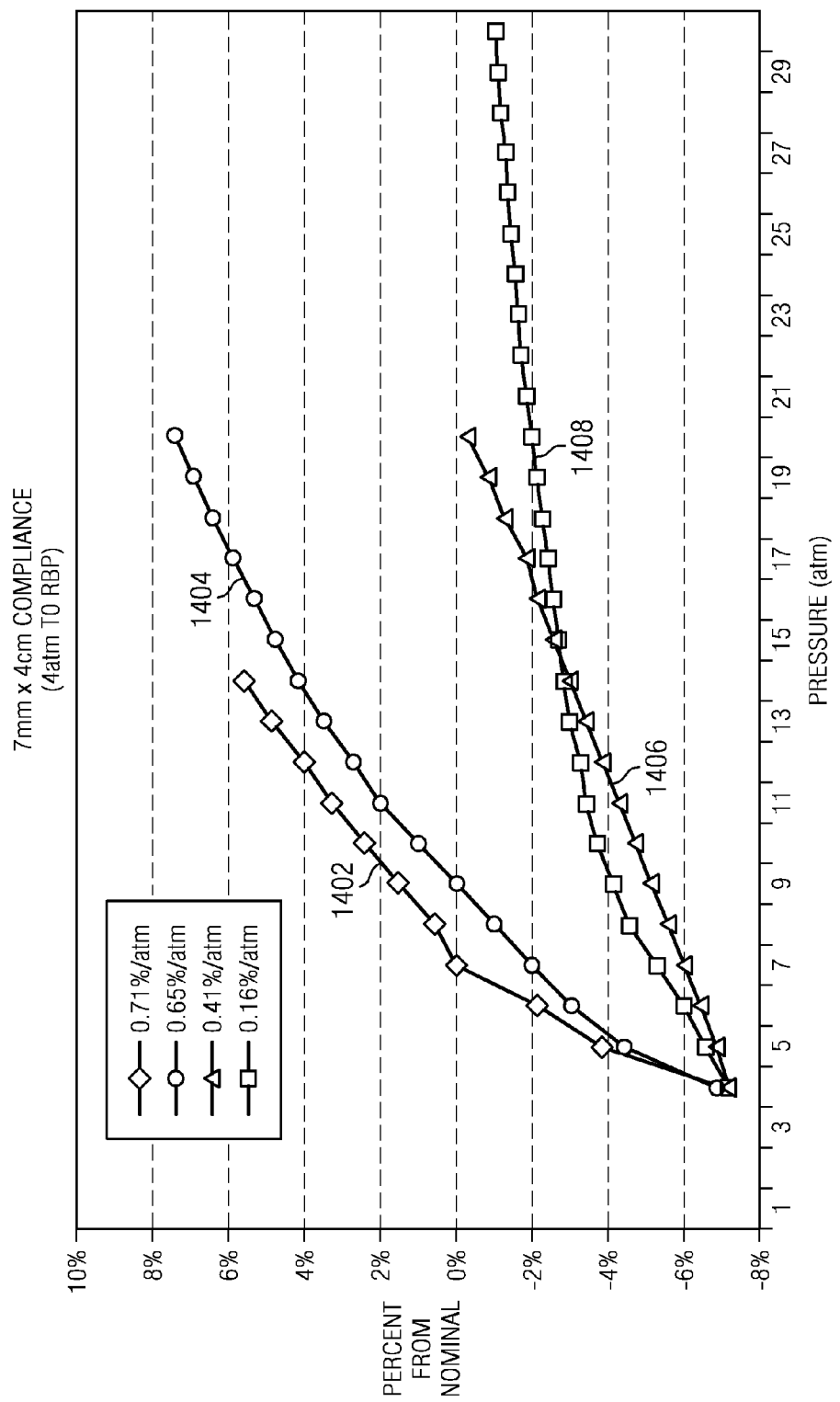
FIG. 14 is a graph illustrating the compliance of various medical balloons.

FIG. 14 illustrates expansion curves for various 7 millimeter medical balloons as the balloons inflate from 4 atmospheres to the balloon's respective rated burst pressures. Line 1402 represents a conventional non-reinforced nylon balloon having a rated burst pressure of 14 atmospheres, Line 1404 represents a semi-compliant fiber-reinforce balloon according to the disclosure of the present application. Line 1406 illustrates the expansion a conventional, non-reinforced PET balloon having a rated burst pressure of 20 atmospheres. Line 1408 represents the expansion of a non-compliant, fiber-reinforced PET balloon having a rated burst pressure of 30 atmospheres.

As illustrated, line 1402 indicates that the conventional nylon balloon has a compliance of 0.71% expansion/per atmosphere after the balloon reaches its nominal diameter and continues to be pressurized to its rated burst pressure. However, the rated burst pressure of the balloon is only 14 atmospheres. Alternatively, the conventional non-compliant PET balloon and the non-compliant fiber-reinforced PET balloon have compliances of 0.41% expansion/per atmosphere and 0.16% expansion/per atmosphere. In contrast, semi-compliant fiber-reinforce balloon has a compliance of 0.65% expansion/per atmosphere and a burst pressure of 20 atmospheres. Thus, a semi-compliant balloon as described herein provides a moderate degree of expansion from the balloon's nominal dimensions with the rated burst pressure of a conventional non-compliant PET balloon.

Turning to FIG. 15 a medical balloon 1500 may be formed using longitudinally extending, substantially non-elastic fibers 1502 and substantially non-elastic hoop fibers 1504. Fibers 1502 and 1504 are encapsulated between a base balloon 1506 and an outer layer or coating 1508 formed from semi-elastic materials such as nylon and/or PEBAX® brand PEBA. Base balloon 1506 and outer layer 1508 may be formed as previously described. Referring to FIG. 15A, hoop fibers 1504 are loosely applied to a base balloon 1506 in a manner such that the fibers form a plurality of curves or "S-bends" 1510 around the circumference of balloon 1500 in the finished balloon. Alternatively, longitudinal fibers 1502 have been applied to the balloon relatively straight and in a configuration wherein the longitudinal fibers will be taut when the balloon reaches its fully inflated state.

When balloon 1500 is inflated, hoop fibers 1504 gradually straighten allowing balloon 1500 to expand radially as indicated by arrow 1512 while longitudinally extending fibers 1502 restrain expansion of the balloon in a longitudinal direction. When substantially inelastic hoop fibers 1504 straighten and become taut as illustrated in FIG. 15B, the hoop fibers constrain further radial expansion of balloon 1500.

Turning to FIG. 16, in one embodiment, a medical balloon 1600 may be constructed with loosely applied looped or slack substantially inelastic longitudinal fibers 1604 and straight, relatively taught substantially inelastic hoop fibers 1602. In this variation, substantially inelastic hoop fibers 1604 constrain further radial expansion of balloon 1600 after the balloon reaches a fully inflated state, while looped or slack longitudinal fibers 1604 permit moderate additional expansion as the balloon is further pressurized, until the longitudinal fibers become taut.

Referring to FIG. 17, in yet another embodiment, a balloon 1700 may be constructed with substantially inelastic longitudinal fibers 1704 and substantially inelastic hoop fibers 1702. As illustrated, fibers 1702 and 1704 are loosely applied to a base balloon 1706 and encapsulated between the balloon and an outer layer 1708. As balloon 1700 is inflated beyond a fully inflated state, substantially inelastic fibers 1702 and 1704 become taut, constraining further expansion of the balloon in the radial and longitudinal directions.

It will be appreciated by those skilled in the art having the benefit of this disclosure that this semi-compliant medical balloon provides a semi-compliant medical balloon having an expansion rate of from about 0.5% expansion/per atmosphere and 1.0% expansion/per atmosphere when pressurized beyond the pressure it reaches its nominal diameter to the balloon's rated burst pressure. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A semi-compliant fiber-reinforced medical balloon that may be inflated and deflated, and when inflated exhibits a moderate change in radial distension across a predetermined range of internal pressures, the balloon comprising:
   a base balloon formed from a semi-elastic polymer material having an elongation to break of from about 10% to about 20%;
   a first fiber layer disposed over the base balloon, the fibers of the fiber layer having an elongation to break of from about 10% to about 20%;
   an outer layer formed from a semi-elastic polymer material having an elongation to break of from about 10% to about 20%; and
   wherein the semi-compliant fiber-reinforced balloon has a rated burst pressure of at least 15 atmospheres and exhibits a compliance in the radial direction of from 0.5% expansion per atmosphere to about 1.0% expansion per atmosphere when pressurized from a fully inflated diameter to the rated burst pressure of the balloon.

2. The semi-compliant fiber-reinforced medical balloon of claim 1 wherein the first fiber layer comprises a plurality of substantially semi-elastic fibers extending along a longitudinal axis of the balloon, the fibers being substantially equally spaced apart around a perimeter of the balloon.

3. The semi-compliant fiber-reinforced medical balloon of claim 2 wherein the fibers of the first fiber layer have a thickness from about 0.0005 to about 0.025 inch and width-to-thickness ratio in the range from about 25:1 to about 45:1.

4. The semi-compliant fiber-reinforced medical balloon of claim 2 further comprising a second fiber layer disposed over the first fiber layer, the second fiber layer comprising semi-elastic fibers hoop fibers wrapped circumferentially around the balloon and wherein the hoop fibers are substantially transverse to the longitudinal axis of the balloon.

5. The semi-compliant fiber-reinforced medical balloon of claim 1 wherein the first fiber layer comprises one of a woven, knitted, non-woven or braided fiber material.

6. The semi-compliant fiber-reinforced medical balloon of claim 5 further comprising a second fiber layer disposed over the first fiber layer, the second fiber layer comprising semi-elastic fibers hoop fibers wrapped circumferentially around the balloon and wherein the hoop fibers are substantially transverse to the longitudinal axis of the balloon.

7. The semi-compliant medical balloon of claim 5 further comprising a second fiber layer disposed over the first fiber layer, the second fiber layer comprising one of a woven, knitted, non-woven or braided fiber material.

8. A fiber-reinforced medical balloon that may be inflated and deflated, the balloon comprising:
   a first fiber layer, the fibers of the first fiber layer being substantially inelastic and extending along a longitudinal axis of the balloon, the fibers of the first fiber layer being substantially equally spaced apart around a circumference of the balloon;
   a second fiber layer disposed over the first fiber layer, the fibers of the second fiber layer being semi-elastic and having an elongation to break of from about 10% to about 20%;
   an outer layer formed from a semi-elastic polymer material having an elongation to break of from about 10% to about 20%; and
   wherein the balloon has a rated burst pressure of at least 15 atmospheres and exhibits a compliance of from 0.5% expansion per atmosphere to about 1.0% expansion per atmosphere in a radial direction when pressurized from a fully inflated diameter to the rated burst pressure of the balloon.

9. The fiber-reinforced medical balloon of claim 8 wherein the second fiber layer comprises semi-elastic hoop fibers wrapped circumferentially around the and wherein the hoop fibers are substantially transverse to the longitudinal axis of the balloon.

10. The fiber-reinforced medical balloon of claim 8, wherein the second fiber layer comprises semi-elastic hoop fibers wrapped circumferentially around the balloon and wherein the hoop fibers are substantially transverse to the longitudinal axis of the balloon.

11. The fiber-reinforced medical balloon of claim 8 wherein the fibers of the first fiber layer and second fiber layer have a thickness from about 0.0005 to about 0.025 inch and width-to-thickness ratio in the range from about 25:1 to about 45:1.

12. The semi-compliant fiber-reinforced medical balloon of claim 8 wherein the second fiber layer comprises one of a woven, knitted, non-woven or braided fiber material.

13. The fiber-reinforced medical balloon of claim 8 wherein the fibers of the first and second fiber layers are encapsulated in a continuous polymer matrix.

14. The fiber-reinforced medical balloon of claim 8 wherein the balloon has a folded wall thickness of from about 0.0010 to about 0.0060 inches.

15. A fiber-reinforced semi-compliant medical balloon that may be inflated and deflated, the balloon comprising:
   at least one fiber layer, the fibers of the fiber layer being semi-elastic and having an elongation to break of from about 10% to about 20% and wherein the fibers of the fiber layer are encapsulated in a continuous polymer matrix such that the angles between the fibers do not change as the balloon is inflated and deflated;
   an outer layer formed from a semi-elastic polymer material having an elongation to break of from about 10% to about 20%; and
   wherein the balloon has a rated burst pressure of at least 15 atmospheres and exhibits a compliance of from 0.5% expansion per atmosphere to about 1.0% expansion per atmosphere in a radial direction when pressurized from a fully inflated diameter to the rated burst pressure of the balloon.

16. The semi-compliant fiber-reinforced medical balloon of claim 15 further comprising first and second fiber layers, the fibers of the first fiber layer along a longitudinal axis of the balloon, the fibers of the first fiber layer being substantially equally spaced apart around a circumference of the balloon, the fibers of the second fiber layer comprising semi-elastic fibers hoop fibers wrapped circumferentially around the balloon and wherein the hoop fibers are substantially transverse to the longitudinal axis of the balloon.

17. The semi-compliant fiber-reinforced medical balloon of claim 15 further comprising first and second fiber layers, wherein the first fiber layer is one of a one of a woven, knitted, non-woven or braided fiber material and wherein the second fiber layer comprises semi-elastic fibers hoop fibers wrapped circumferentially around the balloon and wherein the hoop fibers are substantially transverse to the longitudinal axis of the balloon.

18. The semi-compliant fiber-reinforced medical balloon of claim 17 wherein the fibers of the second fiber layer have an elongation to break of from about 10% to about 20%.

19. The semi-compliant fiber-reinforced medical balloon of claim 17 wherein the fibers of the first and second fiber layers are encapsulated in a continuous polymer matrix.

20. The semi-compliant fiber-reinforced medical balloon of claim 17 wherein the fibers of the first and second fiber layers have a thickness from about 0.0005 to about 0.025 inch and width-to-thickness ratio in the range from about 25:1 to about 45:1.

* * * * *